United States Patent [19]
Chen

[11] Patent Number: 5,098,048
[45] Date of Patent: Mar. 24, 1992

[54] GUIDING CATHETER STABILIZER

[76] Inventor: Chiayu Chen, 2001 N. Adams St. #333, Arlington, Va. 22201

[21] Appl. No.: 195,302

[22] Filed: May 18, 1988

[51] Int. Cl.⁵ .............................................. A61M 5/00
[52] U.S. Cl. .................................... 248/74.2; 248/65; 128/DIG. 26
[58] Field of Search ............... 248/65, 52, 67.7, 74.2, 248/316.8, 121, 75, 76, 80, 105; 128/DIG. 26; 604/180, 179, 174

[56] References Cited

U.S. PATENT DOCUMENTS

| | | | |
|---|---|---|---|
| 2,525,398 | 10/1950 | Collins | 604/179 |
| 3,288,137 | 11/1966 | Lund | 604/180 X |
| 3,630,195 | 12/1971 | Santomieri | 248/74.2 X |
| 3,702,612 | 11/1972 | Schlesinger | 248/74.2 X |
| 4,141,524 | 2/1979 | Corvese, Jr. | 248/74.2 X |
| 4,250,080 | 2/1981 | Gordon | 604/180 |
| 4,576,589 | 3/1986 | Kraus et al. | 128/DIG. 26 |
| 4,606,735 | 8/1986 | Wilder et al. | 248/74.2 X |
| 4,707,906 | 11/1987 | Posey | 248/74.2 X |
| 4,711,636 | 12/1987 | Bierman | 604/180 |

Primary Examiner—Karen J. Chotkowski
Attorney, Agent, or Firm—Wood, Herron & Evans

[57] ABSTRACT

A standard angioplasty Y-connector is secured to a support structure to enable a physician to manipulate the screw cap of the Y-connector and control the passage of the balloon catheter and guiding catheter with one hand. The securing means comprises a "L" shaped main body. First and second mounting members on the short end of the "L" secure the Y-connector position it above the main body. The main body is placed on the patient and the brackets elevate the screw cap above the patient and the physician operates the screw cap with his index finger and thumb. The remaining fingers are placed over the other edge of the Y-connector on the long arm to increase the stability of his grip upon the screw cap.

2 Claims, 2 Drawing Sheets

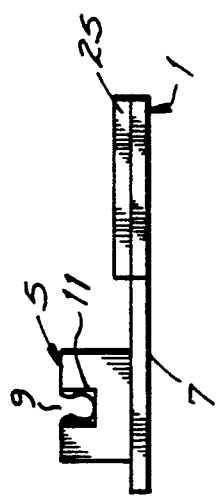
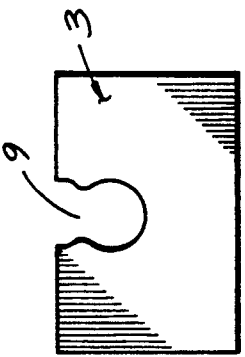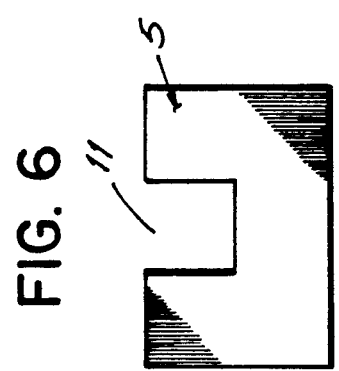
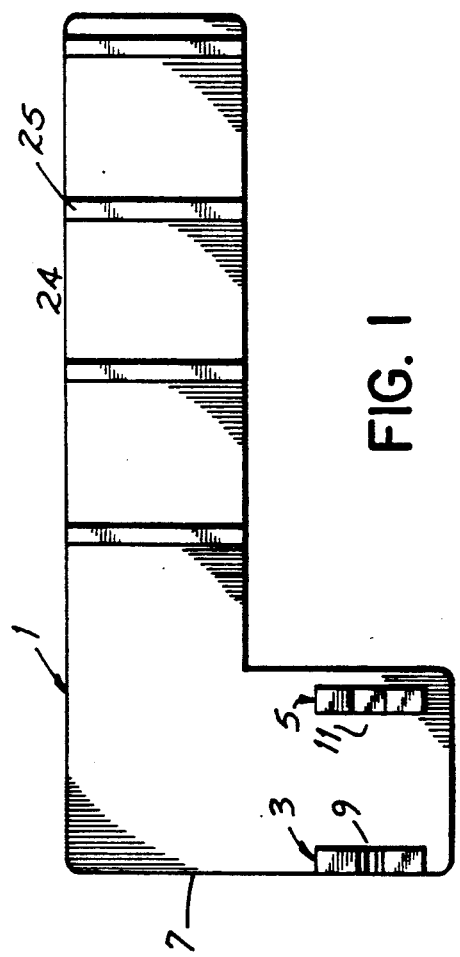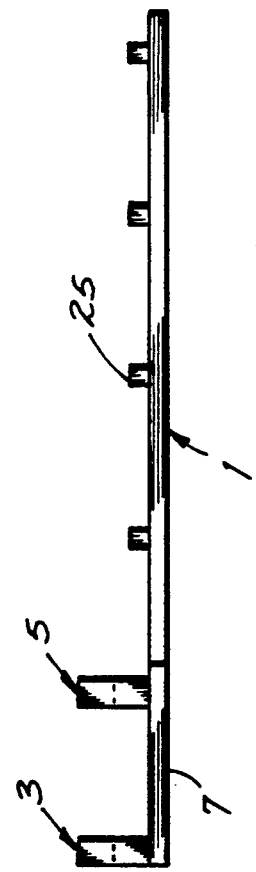

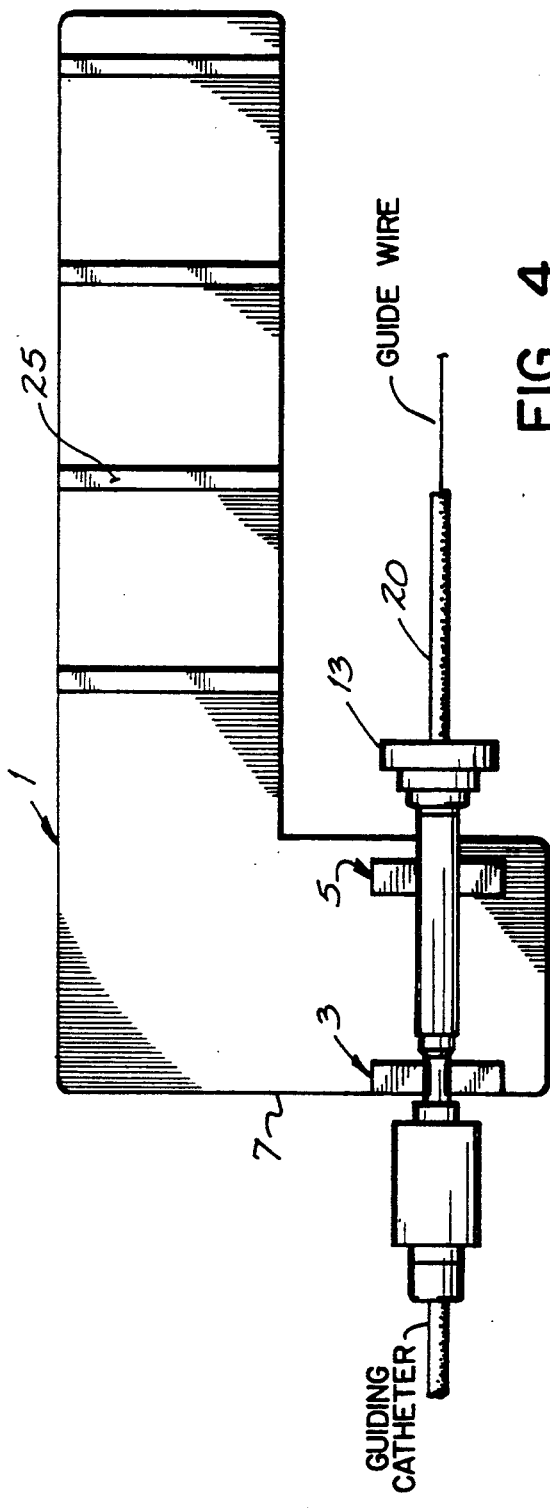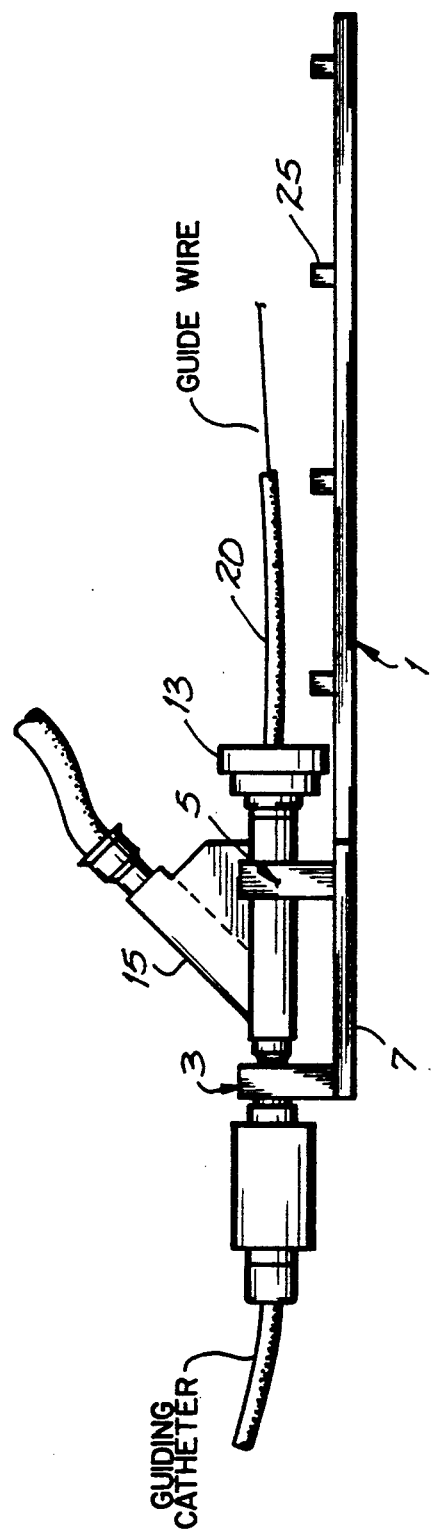

1

GUIDING CATHETER STABILIZER

BACKGROUND OF THE INVENTION

The present invention relates to a guiding catheter stabilizer for use in Percutaneous Transluminal Coronary Angioplasty or Peripheral Vascular Angioplasty.

Percutaneous Transluminal Coronary Angioplasty and Peripheral Vascular Angioplasty have increased in frequency and effectiveness over the last several years—more challenging and complex procedures are being completed successfully as physicians gain confidence in the procedure and the equipment improves. Presently, the equipment used in angioplasty procedures includes three basic components: a guiding catheter, a balloon dilation catheter, and a guide wire. The guiding catheter is inserted in the femoral artery through a short arterial sheath. Attached to the end of the guiding catheter is a Y-connector that allows for passage of both the balloon catheter, and for dye injections to aid in fluoroscopic placement of the balloon at the level of the stenosis to be dilated. Attached to the end of the balloon catheter is another Y-connector through which the guide wire is inserted and additional dye injections can be made.

The normal procedure is to advance the guiding catheter to the ostium of the artery to be dilated and then advance the guide wire across the stenosis into the distal artery. Using the guiding catheter and guide wire as support, the balloon catheter is then advanced through the artery, to the level of the stenosis. The balloon is then inflated to dilate the atherosclerotic plaque.

A problem arises when there is difficulty seating the guiding catheter in the ostium of the artery or when a tight stenosis requires transmission of substantial force from the femoral artery for advancement of the balloon catheter across the stenosis. In this situation, the operator needs to firmly grip the guiding catheter at the femoral artery site with the left hand and advance the balloon with the right hand. The result is that the guiding catheter bends and is ineffective at transferring force for advancement of the balloon catheter across the stenosis.

SUMMARY OF THE INVENTION

The foregoing problem is solved in the present invention by immobilizing the guiding catheter without hendering necessary torquing or manipulation, which allows for the one-handed operation of the balloon catheter and Y-connector. Consequently, the present invention allows a single person to perform the angioplasty procedure in certain situations, where heretofore two persons were necessary, since the balloon catheter can be manipulated with one hand, while the other hand manipulates the guide wire. The additional flexibility is extremely helpful in difficult angioplasty cases and ultimately may result in an improved outcome of the angioplasty procedure.

Specifically, the present invention comprises means for securing and positioning a standard angioplasty Y-connector to a support structure so that the physician ca manipulate the screw cap of the Y-connector and control the passage of the balloon catheter and guiding catheter with one hand. The securing means comprises a "L" shaped main body. The positioning means comprises first and second members on a short end of the "L", which immobilize the Y-connector above the main body. The main body is placed on the patient and since the screw cap is fixed in a position above the patient, the physician can manipulate the screw cap with his index finger and thumb. The remaining fingers are placed over the other edge of the Y-connector on the long arm of the L-shaped main body to increase the stability of the manipulation of the Y-connector. The present invention can be made of Plexiglas ® or pressure molded plastic and is preferably disposable after a single use.

BRIEF DESCRIPTION OF THE DRAWINGS

FIG. 1 shows a top view of the support structure according to the present invention;

FIG. 2 shows a side view of the support structure shown in FIG. 1 along the short side of the "L";

FIG. 3 shows a front view of the support structure shown in FIG. 1;

FIG. 4 shows a top view of the support structure shown in FIG. 1 having a Y-connector mounted thereon;

FIG. 5 shows a side view of the support structure as shown in FIG. 2 with a Y-connector in place;

FIG. 6 shows detail of the first mounting bracket for the support structure shown in FIGS. 1-5; and FIG. 7 shows detail of the second support bracket for the support structures shown in FIGS. 1-5.

DETAILED DESCRIPTION OF THE INVENTION

The present invention is described in detail with reference to the drawings. The securing means, that is the main body (1), is comprised of an "L" shaped piece of Plexiglas ®. The positioning means comprises and has two brackets (3,5) located on the short arm (7). These brackets have slots (9) and (11), respectively, for firmly anchoring a standard Y-connector to the main body 1. The brackets also elevate the Y-connector off the patient to ease the manipulation of the Y-connector screw cap (13) that controls the passage of the balloon catheter (20) in the guiding catheter (21). The brackets can be designed so as to accommodate the particular Y-connector being used. Other types of positioning means such as springs, clips or clamps can be used, depending on the type of Y-connector used in a particular angioplasty procedure.

During an angioplasty procedure, a Y-connector is immobilized within the positioning means, i.e., the brackets. After the Y-connector is firmly seated in the brackets, the index finger and thumb of the right hand are used to manipulate the Y-connector screw cap and the balloon catheter. The remaining three fingers are firmly placed on its long arm (15) to increase stability. To further increase stability, the long arm can be provided with finger pads (24).

A PREFERRED EMBODIMENT

The main body (1) was formed from Plexiglas ® sheets 3/16 inches in thickness of opaque. The long arm of the "L" is 6 inches long and 1¼ inches wide, while the short arm of the "L" is 2¾ inches long and 1-7/16 inches wide. Brackets ⅝ inches long and 3/16 inch wide were formed from Plexiglas ® square rods that were cut to the appropriate sizes. Slots for the supporting brackets were first drilled and subsequently filed to the appropriate shapes and dimensions. All the edges were rounded and smoothed with ultra-fine sandpaper. The brackets are then mounted in parallel on the short arm of the "L" 15/16 inch apart and ¼ inch from the end of the short arm with CA-4 Cyanoacrylate adhesive manufactured by the 3M Corporation (St. Paul, Minn.). One inch wide finger pads (24) are provided in the long arm of the "L" by afixing ⅛ inch wide and 3/16 inch high spacers (25) with CA-4 cyanoacrylate adhesive.

The embodiment shown in the Figures is for catheterizing the patient's right femoral artery. A mirror image of the device is used if the left femoral artery is used as the site of catheter entry. In addition, a mirror image of the device would be used for antegrade cannulazation of the right femoral artery for lower extremity angioplasty.

The principles, preferred embodiments, and modes of operation of the present invention have been described in the foregoing specifications. The invention which is intended to be protected herein should not, however, be construed as limited to the particular forms described as these are to be regarded as illustrative rather than restrictive. Variations and changes may be made by those skilled in the art without departing from the spirit of the invention. Accordingly, the foregoing detailed description should be considered exemplary in nature and not as limiting to the scope and spirit of the invention set forth in the appended claims.

What is claimed is:

1. A catheter connector stabilizer comprising:
an L-shaped plate having a connector-receiving arm and a stabilizer arm at right angles to said connector-receiving arm,
brackets on said connector-receiving arm for holding a connector on said arm,
said finger pads on said stabilizer arm,
whereby a person can, with one hand, hold said stabilizer steady by pressing fingers against it while simultaneously manipulating a catheter or connector with thumb and forefinger.

2. A guiding catheter stabilizer comprising:
an L-shaped plate having a short arm and a long arm;
two brackets at one end of said plate on said short arm for receiving a Y-connector and holding said Y-connector along an axis; and
three finger pads on said long arm, said finger pads being spaced from said brackets and located with respect to said brackets to provide for holding said plate on a patient's body with three fingers while manipulating a catheter or connector with the thumb and index finger, said finger pads being longitudinally spaced from said brackets and laterally spaced from said axis.

* * * * *